US009168551B2

(12) United States Patent
Heisel et al.

(10) Patent No.: US 9,168,551 B2
(45) Date of Patent: Oct. 27, 2015

(54) DISCHARGING APPARATUS FOR MEDIA

(75) Inventors: Thomas Heisel, Singen (DE); Joerg Kohnle, Villingen-Schwenningen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 14/234,167

(22) PCT Filed: Jun. 18, 2012

(86) PCT No.: PCT/EP2012/061572
§ 371 (c)(1),
(2), (4) Date: Jan. 22, 2014

(87) PCT Pub. No.: WO2013/013892
PCT Pub. Date: Jan. 31, 2013

(65) Prior Publication Data
US 2014/0131388 A1 May 15, 2014

(30) Foreign Application Priority Data
Jul. 27, 2011 (DE) .................... 10 2011 079 950

(51) Int. Cl.
*A61M 11/00* (2006.01)
*B05B 11/00* (2006.01)
(Continued)

(52) U.S. Cl.
CPC .......... *B05B 11/3052* (2013.01); *A61M 15/008* (2014.02); *A61M 15/009* (2013.01);
(Continued)

(58) Field of Classification Search
CPC ................................. B67D 7/22; A61M 11/00
USPC .................... 222/36, 38, 182–183; 604/21; 128/203.12, 203.15, 203.23, 200.12, 128/200.23–200.24, 205.23; 377/6, 13, 377/15–16
See application file for complete search history.

(56) References Cited

U.S. PATENT DOCUMENTS

| 2,239,717 | A | * | 4/1941 | Pierce et al. .................. 369/148 |
| 5,755,218 | A | * | 5/1998 | Johansson et al. ........ 128/200.14 |
| 5,809,997 | A | * | 9/1998 | Wolf ........................ 128/200.23 |
| 6,029,659 | A | * | 2/2000 | O'Connor ................ 128/203.12 |
| 8,240,301 | B2 | * | 8/2012 | Spaargaren et al. ...... 128/200.23 |
| 8,739,790 | B2 | * | 6/2014 | Bruna ....................... 128/205.23 |

(Continued)

FOREIGN PATENT DOCUMENTS

EP  1 559 083 B1  8/2005
WO  WO 2007/137991 A1  12/2007

OTHER PUBLICATIONS

Form PCT/ISA/210 International Search Report issued in International Application No. PCT/EP2012/061572 with English translation, date of mailing Oct. 2, 2012 (6 pages).

*Primary Examiner* — Paul R Durand
*Assistant Examiner* — Andrew P Bainbridge
(74) *Attorney, Agent, or Firm* — Flynn, Thiel, Boutell & Tanis, P.C.

(57) ABSTRACT

Discharging apparatus for liquid, pasty or pulverulent media having a housing, a discharging opening, a reservoir for storing the medium prior to being discharged, and a handle which causes medium to be delivered from the reservoir to the discharging opening, wherein the discharging apparatus has an electric load and a converter for converting the mechanical energy introduced at the handle into electrical energy for supplying the electric load.

Mechanical energy introduced at the handle is fed to the converter by a transmission unit. The linear movement of the handle or of a stressing member of a spring energy store, which can be subjected to stressing by means of the handle, is converted into a non-rotary oscillating movement of a pendulum member, wherein the converter is designed for converting the mechanical energy of the oscillating pendulum member into electrical energy.

11 Claims, 4 Drawing Sheets

(51) Int. Cl.
*A61M 15/00* (2006.01)
*B05B 12/00* (2006.01)
*H02K 7/18* (2006.01)
*H02K 35/02* (2006.01)

(52) U.S. Cl.
CPC .............. *B05B11/308* (2013.01); *B05B 12/004* (2013.01); *H02K 7/1892* (2013.01); *H02K 35/02* (2013.01); *A61M 2205/825* (2013.01); *B05B 11/0037* (2013.01)

(56) References Cited

U.S. PATENT DOCUMENTS

| | | | |
|---|---|---|---|
| 2006/0011651 A1* | 1/2006 | Bruna | 222/36 |
| 2007/0017506 A1* | 1/2007 | Bell et al. | 128/200.23 |
| 2007/0135756 A1* | 6/2007 | Kohlbrenner et al. | 604/21 |
| 2008/0185395 A1* | 8/2008 | Sahud | 222/36 |
| 2009/0151721 A1* | 6/2009 | Spaargaren et al. | 128/203.12 |
| 2009/0200983 A1* | 8/2009 | Dyer et al. | 320/107 |

* cited by examiner

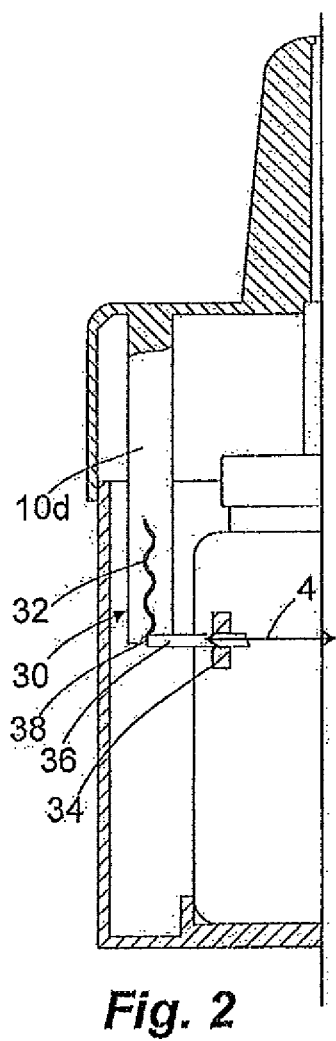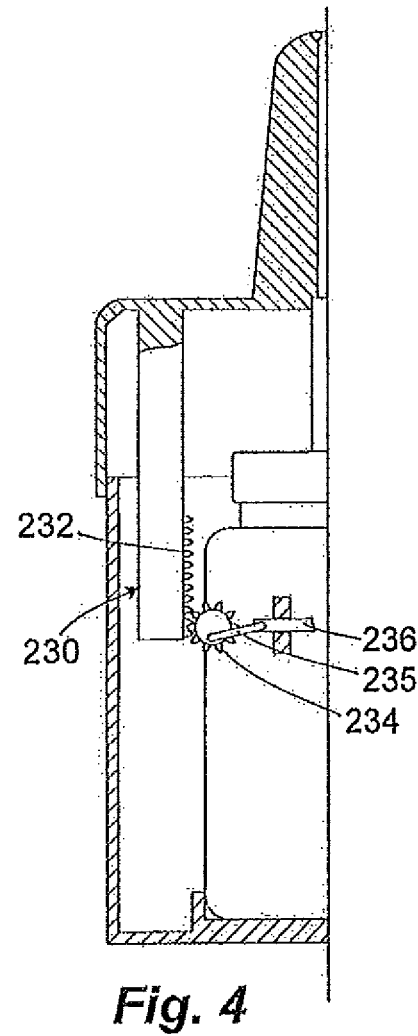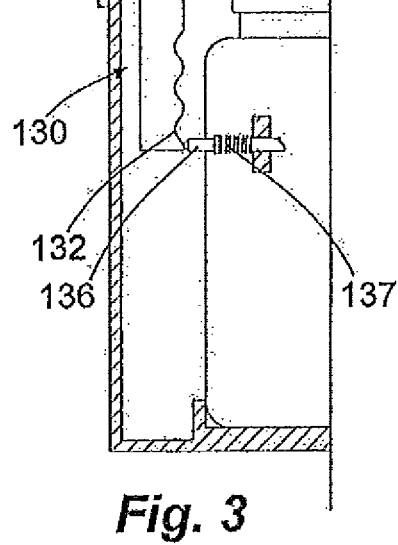

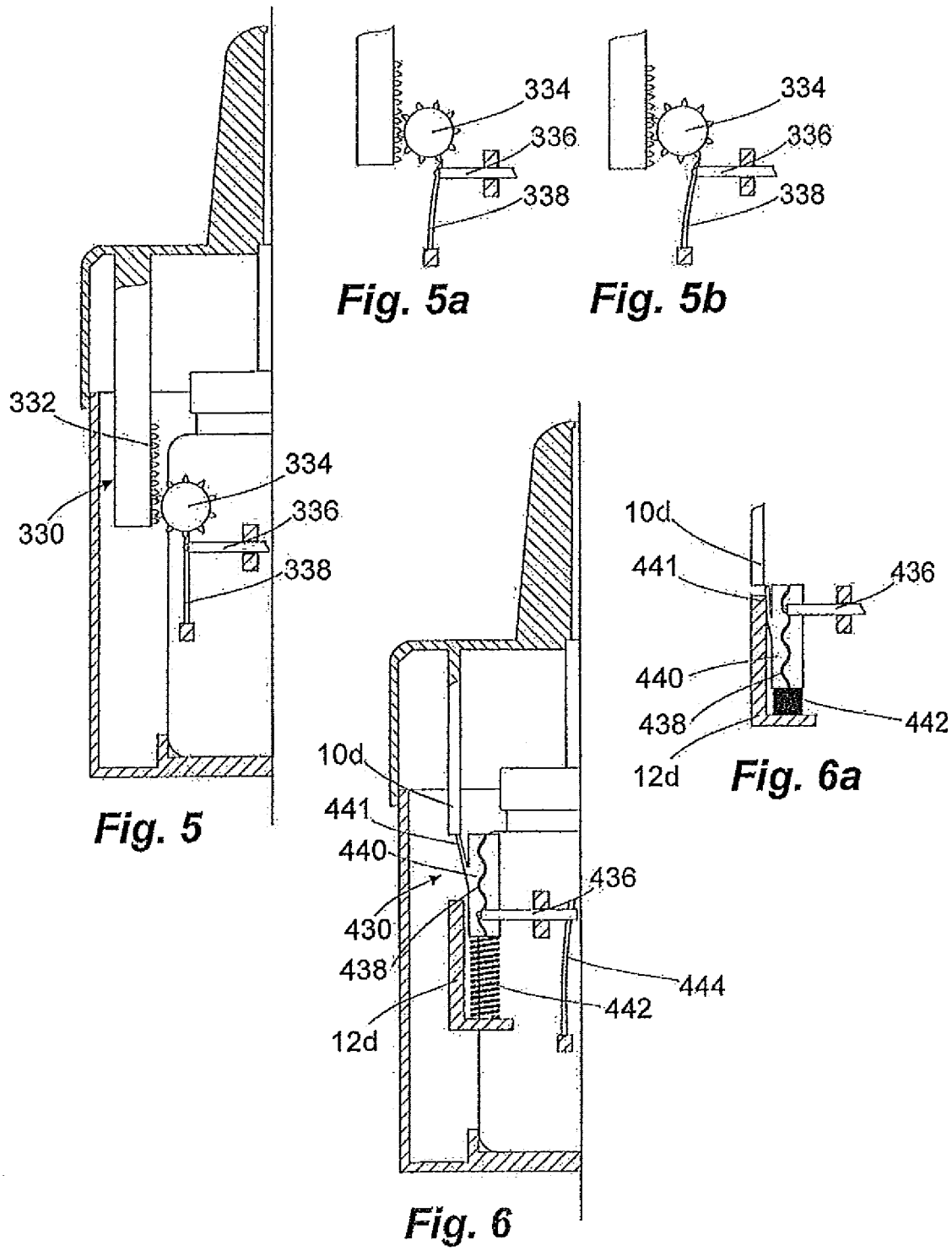

DISCHARGING APPARATUS FOR MEDIA

APPLICATION AREA AND PRIOR ART

The invention relates to a discharging apparatus for liquid, pasty or pulverulent media, having a housing, having a discharging opening for discharging the medium, having a reservoir for storing the medium prior to being discharged, and having a handle, which can be moved linearly in relation to the housing and, by way of a manually induced displacement movement, causes medium to be delivered from the reservoir to the discharging opening. The discharging apparatus here has an electric load. The discharging apparatus also has a converter, by means of which the mechanical energy introduced at the handle is converted, at least in part, into electrical energy for supplying the electric load.

Discharging apparatuses of the type in question are known in the form of dispensers for cosmetic and pharmaceutical media. These are usually portable dispensers which are filled in particular as a dispenser with a pharmaceutical medium and allow a patient to administer said medium.

It is becoming increasingly customary for dispensers to have an electric load, which may be, for example, an electronic counter in the form of a microprocessor and/or electronic indicators such as displays or LEDs. Other electronic components such as, for example, radio transmitters or blocking mechanisms, which prevent further administration of a medicament for a certain period of time, are also known from the prior art. The solution selected most in the prior art for the purpose of supplying the electric load is that of an energy store in the form of a (storage) battery which is charged on delivery.

The prior art, however, has likewise disclosed configurations in which, instead of such a pre-charged energy store, the means provided for generating electrical energy are in the form of the converters mentioned in the introduction. These utilize the mechanical energy which is introduced by the user, by moving the handle, and convert some of said mechanical energy into electrical energy. The energy efficiency here is indeed low. In a corresponding design of the electrical components, however, this energy may be sufficient in order, for example in reaction to a discharging operation, to advance an electronic counter and indicate on a liquid-crystal display the value which is being set in the process.

EP 1 559 083 B1 discloses a dispenser in which, during actuation, a striking pin strikes a piezoelectric element in the actuating direction in order thereby to generate electrical energy. The striking pin here is shifted as a result of mechanical energy which is introduced into it via the actuation of the dispenser. The movement of the striking pin here is linear.

WO 2007/137991 A1 discloses the use of a rotary-operation converter. WO 2007/137991 A1 proposes, for this purpose, a generator which has a pinion which is driven by means of a linearly movable rack.

These known converters for generating electrical energy, and the coupling thereof to the respective actuating handle, are not considered to be ideal since, with the kind of movement direction in question, there is not much flexibility as far as converter selection is concerned. It is also the case that the amount of electrical energy yielded, depending on the amount consumed by the electrical components, is too low.

OBJECT AND SOLUTION

It is an object of the invention to develop a discharging apparatus of the type in question to the extent that it can better generate electrical energy.

According to the main aspect of the present invention, this is achieved in that the mechanical energy introduced at the handle is fed to the converter by a transmission unit, by means of which the linear movement of the actuating handle or of a stressing member of a spring energy store, which can be subjected to stressing by means of the handle, is converted into a non-rotary oscillating movement of a pendulum member, wherein the converter is designed for converting the mechanical energy of the oscillating pendulum member directly or indirectly into electrical energy.

A discharging apparatus according to the invention thus has, in a manner corresponding to a discharging apparatus of the type in question, the components, in the form of the reservoir and of a discharging opening, which are necessary for discharging the medium directly, wherein the medium can be delivered from the reservoir to the discharging opening by the linearly movable handle, preferably by means of a pump coupled to the handle. Alongside the pumping device, however, other configurations are also conceivable, for example one in which the medium, prior to being discharged, is already subjected to pressure and in which an outlet valve in the connecting channel between the reservoir and discharging opening is opened upon actuation of the handle. In addition to these features, which are generally known for discharging apparatuses, the aforementioned at least one electric load is provided, and this may be designed, for example, as a display, as an LED or as a microprocessor. It is preferable for a plurality of electric loads to be provided, these performing various functions together. The converter, which is already known in general terms from dispensers of the type in question, supplies the at least one electric load with electrical energy, this supply preferably not taking place directly. Instead, it is possible to provide components for adapting the voltage. It is also possible to provide a storage device, for example a capacitor, for storing the electrical energy briefly on an interim basis. The discharging apparatus according to the invention may, furthermore, also have a storage battery for longer-term storage of electrical energy. In the case of such a configuration, said storage battery can be utilized directly for supplying the at least one electric load and, for its part, can be charged by the converter.

The converter, according to the first aspect of the invention, is designed for converting the mechanical energy of an oscillating pendulum member into electrical energy. This pendulum member is coupled to the handle by means of a transmission unit such that it is moved back and forth between two end positions a number of times during a displacement movement of the handle. Such a pendulum movement makes it possible to use converters which, if coupled directly in a non-oscillating manner to the actuating handle, would not supply a sufficient quantity of energy. For a configuration according to the invention, use can be made in particular of converters which convert an oscillating linear movement into electrical energy.

The transmission unit can be coupled to the pendulum member such that, in reaction to a displacement movement of the handle, it forces both the movement of the pendulum member in the direction of a first end position and the following movement of the pendulum member into the opposite, second end position. It may also be expedient, however, for the pendulum member to be deflected just in one direction by the transmission unit, and for the following movement of the pendulum member in the opposite direction to be brought about by means of a spring device assigned to the pendulum member. In the case of a pendulum member which is designed for oscillating bending deflection in reaction to actuation of the handle, said spring device may also be provided for by the elasticity of the pendulum member itself.

The gear mechanism can convert the movement of the actuating handle directly into the movement of the pendulum member, and therefore a slowing down of the actuation of the handle also causes the movement of the pendulum member to slow down. Since, depending on the converter, it may be desired to have high movement speeds of the pendulum member and/or a certain speed of the pendulum member, it is nevertheless also possible, in the case of a development, for the spring energy stored to be designed with the stressing member, which has already been mentioned above and can be moved in relation to the housing, and a spring, which acts between the housing and the stressing member. It is provided here that the stressing member is operatively coupled to the handle during the displacement movement, and this therefore subjects the spring to stressing, that furthermore, in the stressed state of the spring, the stressing member is uncoupled automatically from the handle, and this therefore relieves the spring stressing, and that, as the spring is being relieved of stressing, the stressing member is operatively coupled to the pendulum member, at least in certain phases, via the transmission unit, and therefore the movement of the stressing member causes the pendulum member to oscillate. As a result of this configuration, the oscillating movement of the pendulum member is completely independent, at least in certain phases, of the specific type of actuation by the user. The user subjects a spring to stressing during the displacement movement of the handle. As soon as said spring has been subjected to stressing, this gives rise to the stressing member being uncoupled from the handle, preferably in a defined position of the handle relative to the housing, and therefore the stressing member, driven in a reproducible manner by the energy of the spring, is moved back and in the process, via the transmission unit, acts on the oscillating pendulum member. Since the movement of the stressing member is independent of the user-dependent actuating movement, it is thus possible to achieve an oscillating movement at a speed which is ideal for the converter. As an alternative to this configuration, in which the stressing member is coupled to the handle during the displacement movement, it is also possible for the stressing member to be fixed in place in relation to the housing during the displacement movement and for the spring to be provided between the stressing member and the handle, and this therefore likewise results in the spring being subjected to stressing during the displacement movement of the handle. In such a case, when the handle has been pushed, this gives rise to the stressing member being uncoupled from the housing and thus to the desired user-independent movement of the stressing member. Since the housing and the handle are defined merely by their relative movement causing the discharging operation, the terms are freely interchangeable.

A number of configurations are conceivable as far as the transmission unit is concerned. A particularly straightforward possible configuration provides for the linear movement of the actuating handle to be converted into a rotary movement of the gearwheel via a rack. The rotary movement of said gearwheel can then be passed on, via a piston rod, to a linearly movable pendulum member, which is coupled to the converter.

Another configuration provides for the pendulum member to be mounted such that it can be rotated or deflected, in the manner of a bending movement, and for it to interact with a toothing formation or profiling on the handle, on the stressing member or on an intermediate member, which is operatively connected to the handle or to the stressing member, such that the movement of the toothing formation or profiling, for each tooth of the toothing formation or for each profile portion of the profiling, results in the pendulum member coming into engagement with the toothing formation or profiling, being deflected preferably elastically thereby, or rotated counter to the force of a spring, and then coming out of engagement with the toothing formation or profiling again, in which case it springs back into its starting position in order to be moved anew in the same manner by the next tooth or the next profiling.

In the case of such a configuration, the pendulum member is thus repeatedly deflected from a rest position by the profiling or toothing formation until the latter loses contact with the pendulum member and the latter thus springs back into the rest position as a result of an external spring force or its inherent elasticity. In the rest position, the pendulum member is then gripped by the next toothing formation or profiling. Such a configuration is fairly straightforward in structural terms and, if use is made of a piezoelectric bending strip as the converter, allows the oscillating movement of the pendulum member to be used very directly for generating electrical energy.

A further configuration of a transmission unit according to the invention provides for the handle, the stressing member or an intermediate member, which is operatively coupled to the handle or to the stressing member, to have provided on it a curved path, against which butts an extension provided on the pendulum member, and therefore movement of the handle or of the stressing member moves the curved path and the extension is shifted along the curved path, and this causes the pendulum movement of the pendulum member.

In the case of such a configuration, part of the pendulum member which butts against the curved path, or is in engagement with a curved path designed in the form of a guide track, thus follows the curved path on account of limited movement capability provided for the pendulum member, preferably of linear movement capability of the pendulum member, in a direction other than the movement direction of the handle, of the stressing member or of the intermediate member. It is possible for said curved path to be, for example, in the form of a sine curve and thus to move the pendulum member back and forth repeatedly. The curved path may be provided in the form of an undulating edge of a curved-path component, against which the extension of the pendulum member is pushed by means of a spring assigned to the pendulum member. This variant allows particularly straightforward assembly. It is also possible, however, for the curved path to be designed in the form of a groove-like guide track, in which an extension of the pendulum member engages and which thus moves said pendulum member back and forth without any additional spring on the same.

As far as the configuration of the converter for generating electrical energy is concerned, there are a large number of expedient alternatives specific to the application case.

A preferred configuration provides for the converter to be designed as an electromagnetic generator, which has a component with a magnet and a component with a conductor, preferably in the form of a coil, connected to the electric load, wherein one of the components is mounted on the housing, and wherein the other component is provided on the pendulum member. Such an electromagnetic generator can provide electrical energy for the load by way of the pendulum member and the oscillating movement thereof.

An alternative configuration of a converter, which is also understood to be part of the invention in conjunction with a discharging apparatus of the type in question, and therefore without an oscillating pendulum member, has the following components. It has an induction mechanism, which is of elongate design and has a coil wound around it between a first end region and a second end region. Said converter also has a magnet unit with a magnet and a first and a second north-pole surface, provided on the north pole of the magnet, and a first and a second south-pole surface, provided on the south pole of the magnet. The induction mechanism and the magnet unit here can be moved in relation to one another between a first relative position and a second relative position, wherein, in the first relative position, the first end region of the induction mechanism butts against the first north-pole surface and the second end region of the induction mechanism butts against the second south-pole surface and, in the second relative position, the first end region of the induction mechanism butts against the first south-pole surface and the second end region of the induction mechanism butts against the second northpole surface. By actuation of the handle here, the induction mechanism and the magnet unit are shifted between the relative positions one or more times during an actuating displacement.

In the case of a configuration with an oscillating pendulum member, the latter is coupled to the magnet unit or the induction mechanism such that the magnet unit and the induction mechanism are shifted back and forth a number of times in reaction to a displacement movement of the handle. A converter like that described, however, is also suitable for discharging apparatuses in which the induction mechanism and magnet unit, in reaction to a movement of the handle, shifts relative to one another only once, possibly with a single return movement, which can be brought about by a spring provided for this purpose.

The operational principle of the aforementioned converter with induction mechanism and magnet unit is based on the polarity of the two end regions of the magnetic induction mechanism being reversed magnetically in an alternating manner. In the first relative position, the first end region is in contact with the north pole of the magnet unit, whereas the second end region is in contact with the south pole of the magnet unit. In the second relative position, the first end region is in contact with the south pole, whereas the second end region is in contact with the north pole. This polarity reversal of the induction mechanism, which may take place a number of times during actuation of the handle, induces a voltage in a coil which can be used directly or indirectly for supplying power to the electric load. It is not imperative here for the entire induction mechanism to butt against the respective surfaces. A comparable effect can also be achieved by the induction mechanism approaching the respective surfaces in an alternating manner.

In a further variant of a converter, which can likewise be used in conjunction with the aforementioned oscillating pendulum member, but also with a discharging apparatus of the type in question, the converter is a piezoelectric bending transducer of which one end is mounted in the housing and the free end is deflected one or more times by actuation of the handle during an actuating displacement. Such a piezoelectric bending transducer, which may be of bipolar or unipolar design for use according to the invention, is elongate and comprises piezoelectric crystals or has such piezoelectric crystals, in which case the latter are applied to a carrier of the bending transducer. Said piezoelectric crystals are arranged here such that bending of the piezoelectric bending transducer, which is clamped in at one end, in a direction transverse to the main direction of extent thereof generates an electrical voltage. Such a piezoelectric bending transducer can be deflected out and back one or more times by the transmission unit in reaction to an actuating displacement.

It is particularly advantageous if the natural frequency of the piezoelectric bending transducer is taken into consideration here. It is thus possible for the piezoelectric bending transducer to be designed, in particular, as a pendulum member which oscillates in reaction to manual actuation of the handle, wherein the oscillating movement is supplied with mechanical energy by the spring energy store, and wherein the spring of the spring energy store is adapted to the piezoelectric bending transducer such that the latter oscillates at its resonant frequency (±20%) at least in certain phases. Such a configuration thus provides for the abovedescribed uncoupling of the movement of the pendulum member from the movement of the actuating handle, and therefore, irrespective of the actuating handle being moved quickly or slowly, the pendulum member is stimulated with a speed profile which is always the same. This may be based on the aforementioned resonant frequency, and therefore a particularly high energy efficiency is achieved.

As has already been mentioned in the introduction, the movement of the pendulum member is preferably an oscillating linear movement. This oscillating linear movement takes place preferably at right angles to the actuating direction of the handle. In particular in such a case, but also in the case of other oscillating movements of the pendulum member, it is considered to be advantageous if the handle can be moved in relation to the housing in an actuating direction which encloses an angle between 70° and 110° with a main direction of extent of the discharging apparatus, this latter direction being defined by a discharging direction of the medium.

BRIEF DESCRIPTION OF THE DRAWINGS

Further aspects and advantages of the invention can be gathered, not just from the claims, but also from the following description of preferred exemplary embodiments of the invention, which are explained hereinbelow with reference to the figures, in which FIGS. 2 to 6 show different variants of a transmission unit for the discharging apparatus from FIGS. 1a and 1b, and FIGS. 7 to 9 show different variants of a converter for the discharging apparatus from FIGS. 1a and 1b.

DETAILED DESCRIPTION OF THE EXEMPLARY EMBODIMENTS

Figure 1A:
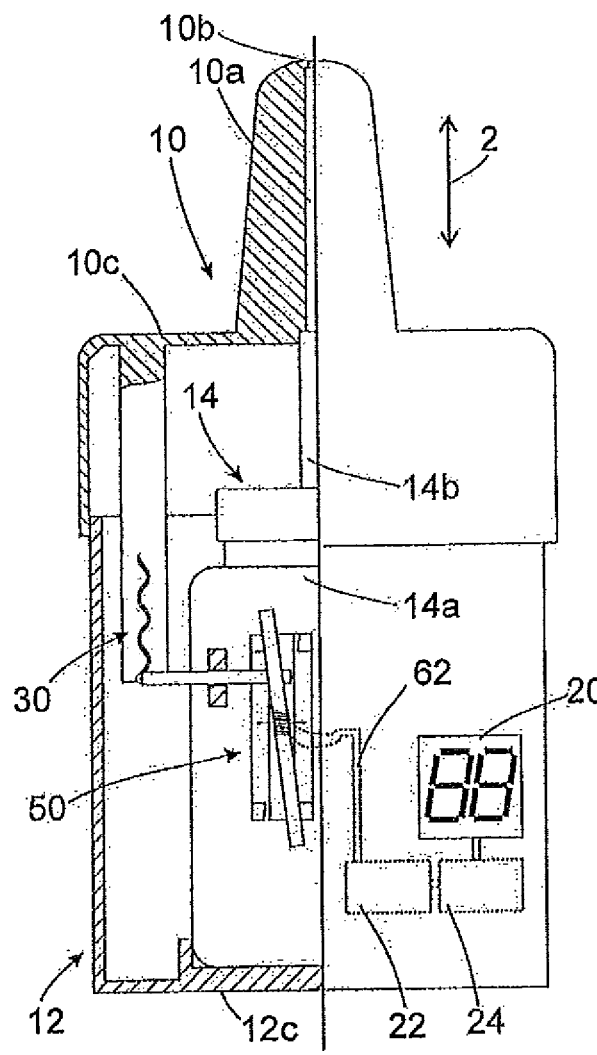
FIGS. 1a and 1b show a discharging apparatus according to the invention in the non-actuated and in the actuated states, with a first variant of a transmission unit and a first variant of a converter for generating electrical energy.
Figure 1B:
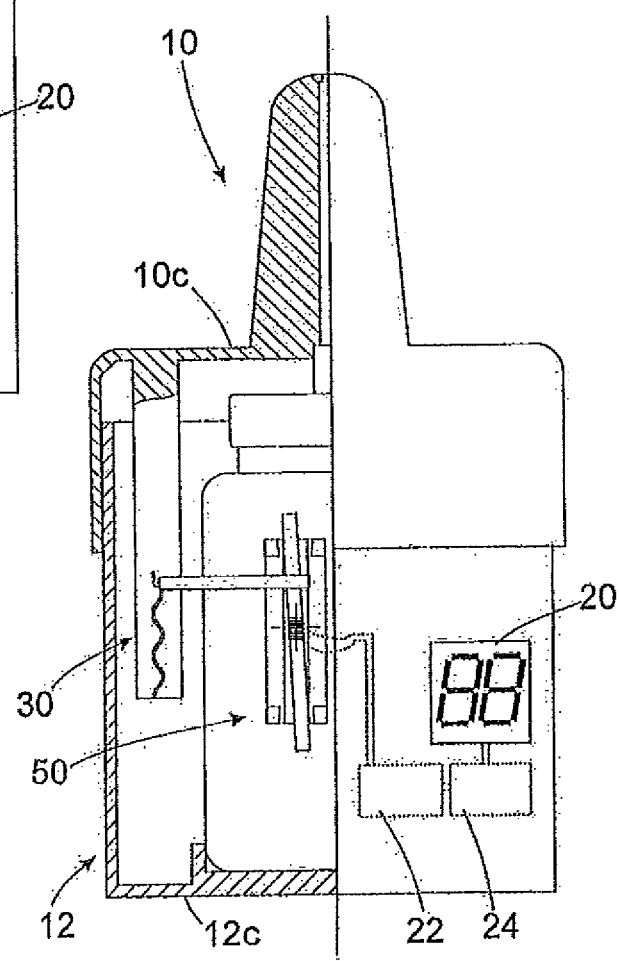

FIGS. 1a and 1b show a discharging apparatus according to the invention in schematically simplified form.

Said discharging apparatus comprises two housing parts 10, 12 which can be shifted for linear movement in relation to one another in the direction of the arrow 2, wherein the upper housing part 10 has a discharging channel 10a and a discharging opening 10b. A housing interior, which is enclosed by the housing parts 10, 12, contains a pumping dispenser 14 with a medium store 14a and an outlet connector 14b. The outlet connector 14b is positioned here such that it opens out into the outlet channel 10a. A discharging operation can be achieved using the discharging apparatus illustrated by the two housing parts 10, 12 having force supplied to them, and thus being pushed one inside the other, in the manner portrayed in FIG. 1b, by actuating surfaces 10c, 12c being subjected to pressure. Consequently, the outlet connector 14b is pushed in the direction of the reservoir 14a of the pumping dispenser 14, as a result of which an outlet valve (not illustrated) of the pumping dispenser 14 is opened and the medium, which is subjected to pressure, is delivered to the discharging opening 10b from the store 14a through the outlet connector 14b. The present configuration thus provides for the medium to be present in a state in which it is already subjected to pressure, and for the actuation to cause the medium to be discharged as a result of the outlet valve being opened. This example, however, is purely by way of example. It could equally be possible to provide a configuration in which shifting of the housing parts 10, 12 results in actuation of a pumping apparatus by means of which medium which is stored in a pressureless state is delivered to the discharging opening 10b.

Figure 8:
Figure 9:
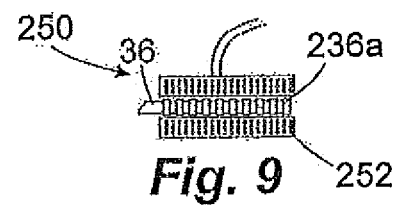

The discharging apparatus illustrated is provided with a counter. For this purpose, it has a liquid-crystal display 20, which is connected to a microprocessor 24 (diagrammatically indicated). The microprocessor 24 and the display 20 are supplied with electrical energy by a buffer store 22 designed in the form of a capacitor. There is no battery provided for supplying the electronic components 20, 24. Instead, the dispenser illustrated is designed such that the electrical energy which is necessary for operating said electronic components at least briefly is recovered from that mechanical energy which is introduced into the system by the user upon actuation of the discharging apparatus. For this purpose, the discharging apparatus has a transmission unit 30, which couples the upper housing part 10 to a converter 50 for generating electrical energy. The transmission unit 30 and alternative transmission units 130, 230, 330, 430 are illustrated on their own in FIGS. 2 to 6. All of these transmission units can be used to equal effect in the discharging apparatus of FIGS. 1a and 1b. The converter 50 and alternative converters 150 and 250 are illustrated in FIGS. 8 to 9. All of these converters can be used to equal effect in the discharging apparatus of FIGS. 1a and 1b. Any desired combinations of the converters and transmission units are also possible and covered by the invention.

The configuration which is used for the exemplary embodiment of FIGS. 1a and 1b is as follows: the transmission unit 30, which is also illustrated separately in FIG. 2, comprises an extension 10d, which is provided on the upper housing part 10 and extends into the interior of the discharging apparatus. Said extension has provided on it a curved path 32, which is designed in the form of a groove and, in the present case, describes the form of a sine curve. The transmission unit 30 also comprises a pendulum member 36, which can be moved linearly, merely in a direction orthogonal to the direction 2, by way of a bearing guide 34 fastened on the lower housing part 12. At the end which is directed towards the curved path 32, the pendulum member 36 has an engagement pin 38, which projects into the curved path 32.

As a result, when the upper housing part 10 is pushed downward, the pendulum member executes an oscillating movement in the direction of the arrow 4 and thus oscillates back and forth a total of three times, in the case of the present exemplary embodiment, between two end positions. The pendulum member 36, in turn, is coupled to the converter 50 for generating electrical energy, said converter being illustrated more precisely in FIG. 7.

Said converter 50 has a rod-like induction mechanism 52, which is mounted such that it can be pivoted about the axis 51. Said induction mechanism is adjacent to a magnet unit 54, which has a permanent magnet 56 with a north-pole side 56a and a south-pole side 56b. These two sides 56a, 56b are each followed by a plate-like body 58, 59 made of magnetizable material. Each of these plates 58, 59 has two north-pole and south-pole extensions 58a, 58b, 59a, 59b. These limit the movement of the induction mechanism 52 between two end positions.

Figure 7:
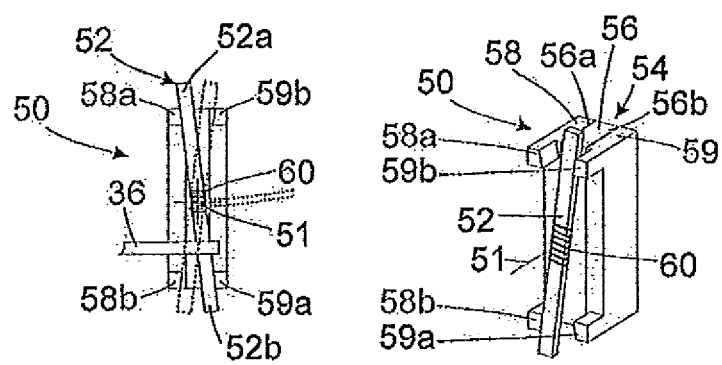

In that end position of the induction mechanism 52 which is not illustrated by dashed lines in the left-hand illustration of FIG. 7, the induction mechanism has an upper end 52a butting against the north-pole extension 58a and its lower end 52b butting against the south-pole extension 59a. It is therefore magnetized correspondingly. If shifting into the opposite end position (illustrated by dashed lines) takes place, then, in this position, the upper end 52a butts against the south-pole extension 59b, whereas the lower end 52b butts against the north-pole extension 58b. In this second end position, the magnetization of the induction mechanism 52 is thus the reverse of the magnetization in the first end position. This change in magnetization of the induction mechanism 52 is utilized, by means of a coil 60 which encloses the induction mechanism 52, in order to induce a current in said coil. Said current is channeled to the buffer store 22 via lines 62. It may also be possible to provide a rectifier, or other sub-devices suitable for converting the current, in between.

The coupling between the transmission unit 30 and the converter 50 is such that the pendulum member 36 causes the aforementioned movement of the induction mechanism 52 between its two end positions. This means that, during an actuating operation of the discharging apparatus, the magnetization of the induction mechanism 52 is changed a number of times and electrical energy is thus recovered, so that the aforementioned electronic components are thus supplied with sufficient energy. The latter can be utilized, for example, in order, by means of the microprocessor 24, to advance a counting register and to indicate the corresponding value briefly on the liquid-crystal display 20, or in the case of a bistable display permanently until the next actuation takes place.

FIGS. 3 to 6 describe alternative transmission-unit configurations which can be used with the converter 50 or the other converters 150, 250, which are yet to be described hereinbelow, or yet other converters.

The configuration of FIG. 3 shows, in contrast to the configuration of FIG. 2, the transmission unit 130 with a curved path 132 which is open at one end. In order for the pendulum member 136 nevertheless to be moved in oscillating fashion, the pendulum member is assigned a restoring spring 137. In respect of FIG. 3, movement of the pendulum member to the right is effected by the curved path 132, whereas the movement to the left is brought about by the spring 137.

In the case of the configuration of FIG. 4, instead of a curved path, a rack 232 is provided at a fixed location on the upper housing part 10, said rack meshing with a gearwheel 234. Said gearwheel is connected to the pendulum member 236 via an eccentrically fitted piston rod 235. Appropriate fitting of the piston rod on the gearwheel 234 makes it possible to set the amplitude of the movement of the pendulum member 236. The frequency can be influenced by virtue of a smaller or larger gearwheel 234 being selected.

The gear mechanism 330 of FIG. 5, once again, has a rack 332 provided, said rack being connected to the housing part 10 and, once again, meshing with a gearwheel 334. In this configuration, however, coupling to the likewise linearly movable pendulum member 336 takes place via a bending strip 338, which has its lower end mounted on the lower housing part 12. In the position illustrated in FIG. 5, when the upper housing part 10 is pushed downward, said bending strip 338 is gripped by a tooth of the gearwheel 334 and deflected in the manner illustrated in FIG. 5a, the bending strip 338 being subjected to bending deformation as a result. In the state which is illustrated in FIG. 5b, the bending strip 338 then comes out of engagement with the aforementioned tooth and, on account of its elasticity, returns into the position of FIG. 5, where it is then gripped again by the next tooth of the gearwheel 334. The pendulum member 336, which is fitted on the bending strip 338, follows this movement. Material properties of the deflecting portion 338 make it possible, in this configuration, to influence the speed of the returning movement between the state of FIG. 5b and the state of FIG. 5. A high modulus of elasticity makes it possible to achieve a very quick and abrupt transfer back, which is suitable, in particular, for attachment to a piezoelectric converter.

In a variant of the embodiment of FIG. 5, it is also possible for the bending strip 338 itself to constitute the converter, by being designed in the form of a piezoelectric bending strip. The repeated deflection thereof results in piezoelectric generation of electrical energy. In the case of such a configuration, the bending strip 338 itself forms the pendulum member. The pendulum member 336 is dispensed with.

The configuration of FIG. 6 is similar to the configuration of FIGS. 1 and 2. A curved path 438 is also provided here, a pendulum member 436 interacting therewith in the same manner as has been described in relation to FIG. 2. The special feature of this configuration is that the curved path 438 is not fixed to the upper housing part 10. While the housing part 10 is being pushed down, a crosspiece 10d, on account of a coupling arm 441 on a vertically movable stressing member 440, does indeed interact with the curved path 438 and carries the same along. At the same time, however, during the pushing-down operation, a spring 442 assigned to the stressing member 440 is subjected to stressing. As soon as the lower end position of the housing part 10 and of the stressing member 440 with the curved path 438 has been reached, the coupling arm 441 is deflected, by way of an uncoupling portion 12d provided on the lower housing part 12, in the manner illustrated in FIG. 6a, and this therefore results in the contact being lost between the extension 10d and the stressing member 440. Consequently, the latter is moved back into the starting position by the stressed spring 442 together with the curved path 438. This movement takes place irrespective of the manner in which the user has pushed down the upper housing part 10. It is therefore possible to oscillate the pendulum member 436 in a manner which is dependent only on structural parameters of the discharging apparatus, and this makes it possible to achieve an oscillation speed which is ideal for the specific converter used. This is of value, for example, when a piezoelectric bending strip 444 interacts with the pendulum member 436 in the manner illustrated by dashed lines in FIG. 6, since using the natural frequency of said bending strip can help minimize mechanical conversion losses.

FIG. 7 shows the already described converter 50, which is based on magnetic pole reversal of an induction mechanism 52.

A conceivable alternative to this, for example, is that configuration of a converter 250 which is illustrated in FIG. 8, and in which the pendulum member 36 executes striking movements against a piezoelectric crystal 152 in reaction to actuation of the discharging apparatus. These striking movements result in the piezoelectric generation of electrical energy.

As a further alternative to this, the configuration of FIG. 9 shows a sectional and schematic view of a linear generator 250. In this case, the pendulum member 36 is designed with permanent magnets 236a and is moved within a coil 252, which remains at a fixed location in relation to the lower housing part 12, a current being generated as a result.

The invention claimed is:

1. A discharging apparatus for liquid, pasty or pulverulent media, having
    a housing;
    a discharging opening for discharging the medium;
    a reservoir for storing the medium prior to being discharged;
    a handle movable linearly in relation to the housing and manually movable along a displacement movement which causes medium to be delivered from the reservoir to the discharging opening;
    an electric load;
    a converter which converts mechanical energy introduced at the handle into electrical energy for supplying the electric load; and
    a transmission unit which feeds the mechanical energy introduced at the handle to the converter, the transmission unit converting linear movement of the handle to a non-rotary oscillating movement of a pendulum member, the converter being designed for converting mechanical energy of the oscillating pendulum member into electrical energy.

2. The discharging apparatus as claimed in claim 1, further including a spring energy store subjected to stressing by manual movement of the handle and having a stressing member movable in relation to the housing, and a spring acting between the housing and the stressing member, the stressing member being operatively coupled to the handle during the displacement movement to subject the spring to stressing, wherein in a stressed state of the spring, the stressing member is uncoupled automatically from the handle to relieve the spring of stressing, and as the spring is being relieved of stressing, the stressing member is operatively coupled to the pendulum member, at least in certain phases, via the transmission unit and movement of the stressing member causes the pendulum member to oscillate.

3. The discharging apparatus as claimed in claim 1, further including a spring energy store subjected to stressing upon movement of the handle along the displacement movement and having a stressing member, the transmission unit including a toothing formation or profiling on one of: the handle; the stressing member; and an intermediate member operatively connected to the handle or to the stressing member, the pendulum member being mounted for deflection and interacting with the toothing formation or profiling such that movement of the toothing formation or profiling, for each tooth of the toothing formation or each profile portion of the profiling, results in the pendulum member coming into direct or operative engagement with the toothing formation or profiling, being deflected and then coming out of direct or operative engagement with the toothing formation or profiling.

4. The discharging apparatus as claimed in claim 1, further including a spring energy store subjected to stressing upon movement of the handle along the displacement movement and having a stressing member, the handle or the stressing member having a curved path against which butts an extension provided on the pendulum member, wherein movement of the handle or of the stressing member moves the curved path and the extension is shifted in the curved path to cause oscillating movement of the pendulum member.

5. The discharging apparatus as claimed in claim 1, wherein the converter is designed as an electromagnetic generator having a component with a magnet and a component with a conductor connected to the electric load, wherein one of the components is mounted on the housing, and the other component is provided on the pendulum member.

6. A discharging apparatus for liquid, pasty or pulverulent media, having
    a housing;
    a discharging opening for discharging the medium;
    a reservoir for storing the medium prior to being discharged;

a handle movable linearly in relation to the housing and manually movable along a displacement movement which causes medium to be delivered from the reservoir to the discharging opening;

an electric load;

a converter which converts mechanical energy introduced at the handle into electrical energy for supplying the electric load, the converter comprising:

an induction mechanism made of a magnetizable material, and a coil wound around the induction mechanism between a first end region of the induction mechanism and a second end region of the induction mechanism; and a magnet unit including a magnet having north and south poles, a first and a second north-pole surface provided on the north pole of the magnet, and a first and a second south-pole surface provided on the south pole of the magnet, the induction mechanism and the magnet unit being movable in relation to one another between a first relative position and a second relative position, wherein in the first relative position the first end region of the induction mechanism butts against the first north-pole surface and the second end region of the induction mechanism butts against the second south-pole surface, and in the second relative position the first end region of the induction mechanism butts against the first south-pole surface and the second end region of the induction mechanism butts against the second north-pole surface, and actuation of the handle shifts the induction mechanism and the magnet unit between the first and second relative positions one or more times during the displacement movement of the handle.

7. A discharging apparatus for liquid, pasty or pulverulent media, having a housing;

a discharging opening for discharging the medium;

a reservoir for storing the medium prior to being discharged;

a handle manually movable linearly in relation to the housing along an actuating displacement movement in which medium is delivered from the reservoir to the discharging opening;

an electric load; and a converter which converts mechanical energy introduced at the handle into electrical energy for supplying the electric load, the converter having a piezoelectric bending transducer with one end clamped in the housing and a free end deflected more than once during the actuating displacement movement of the handle.

8. The discharging apparatus as claimed in claim 7, wherein the piezoelectric bending transducer is designed as a pendulum member which oscillates in reaction to manual movement of the handle, wherein the oscillating movement is supplied with mechanical energy by a spring energy store having a spring adapted to the piezoelectric bending transducer such that the piezoelectric bending transducer oscillates at its resonance frequency at least in certain phases.

9. The discharging apparatus as claimed in claim 1, wherein the handle is movable in relation to the housing in an actuating direction which encloses an angle between 70° and 110° with a main direction of extent of the discharging apparatus, the main direction of extent being defined by a discharging direction of the medium.

10. The discharging apparatus according to claim 1, wherein the converter comprises:

an induction mechanism made of a magnetizable material, and a coil wound around the induction mechanism between a first end region of the induction mechanism and a second end region of the induction mechanism; and a magnet unit including a magnet having north and south poles, a first and a second north-pole surface provided on the north pole of the magnet, and a first and a second south-pole surface provided on the south pole of the magnet, the induction mechanism and the magnet unit being movable in relation to one another between a first relative position and a second relative position, wherein in the first relative position the first end region of the induction mechanism butts against the first north-pole surface and the second end region of the induction mechanism butts against the second south-pole surface, and in the second relative position the first end region of the induction mechanism butts against the first south-pole surface and the second end region of the induction mechanism butts against the second north-pole surface, and actuation of the handle shifts the induction mechanism and the magnet unit between the first and second relative positions one or more times during the displacement movement of the handle.

11. The discharging apparatus according to claim 1, wherein the converter includes a piezoelectric bending transducer having one end clamped in the housing and a free end deflected one or more times by movement of the handle during the displacement movement.

* * * * *